United States Patent [19]

Mayer

[11] 4,275,719
[45] Jun. 30, 1981

[54] APPARATUS AND METHOD FOR PROVIDING AN ASEPTIC SURGICAL ENVIRONMENT

[76] Inventor: Nathan Mayer, 27 Messler St., East Brunswick, N.J. 08816

[21] Appl. No.: 25,333

[22] Filed: Mar. 30, 1979

[51] Int. Cl.³ .................... A61F 13/00; A61B 19/00
[52] U.S. Cl. ................................. 128/132 D; 128/1 R
[58] Field of Search ............... 128/132 D, 132 R, 1 B, 128/1 R, 139, 910, 205.26, 30.2

[56] References Cited

U.S. PATENT DOCUMENTS

| | | | |
|---|---|---|---|
| 3,051,164 | 8/1962 | Trexler | 128/1 B |
| 3,090,694 | 5/1963 | Pereng et al. | 128/132 D |
| 3,236,370 | 2/1966 | Pereny et al. | 128/132 D |
| 3,303,841 | 2/1967 | Dennis | 128/24 |
| 3,492,987 | 2/1970 | Parker | 128/1 R |
| 3,602,212 | 8/1971 | Howorth | 128/1 R |
| 3,692,024 | 9/1974 | Von Otto | 128/132 |
| 3,777,736 | 12/1973 | Van der Waaij et al. | 128/1 R |
| 3,802,416 | 4/1974 | Cazalis | 128/1 R |
| 3,820,536 | 6/1974 | Anspach, Jr. et al. | 128/132 |
| 3,824,987 | 7/1974 | Howorth | 128/1 R |
| 3,881,477 | 5/1975 | Von Otto | 128/132 |
| 3,893,457 | 7/1975 | Van der Waaij | 128/132 R |
| 4,038,974 | 8/1977 | Pielkenrood | 128/1 R |

OTHER PUBLICATIONS

"Plastic Surgical Adhesive Drape", *Ann. Surg.*, Jul. 1976, pp. 46–50.

*Primary Examiner*—Lee S. Cohen
*Assistant Examiner*—C. W. Shedd
*Attorney, Agent, or Firm*—Amster, Rothstein & Engelberg

[57] ABSTRACT

A surgical procedure and apparatus therefor wherein a patient to be operated on is first wrapped with a plastic film sheet which is adhesively sealed to the patient's body remote from an operating area on the body, and is also sealed against an incision site on the body at the operating area. A sterilized atmosphere is provided beneath the film sheet for contacting the patient's skin. Another sterilized atmosphere is provided within a region substantially adjacent the body including the incision site, thereby enabling a surgeon to cut through the film sheet and into the patient's body with minimal risk of infection. Extensive and costly operating room sterilization procedures are thus significantly reduced, and patient comfort, as well as treatment, can be enhanced by controlling the temperature and humidity of the atmosphere provided beneath the film sheet.

10 Claims, 8 Drawing Figures

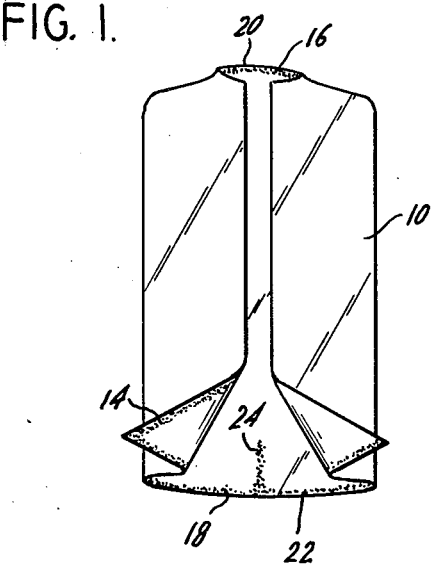
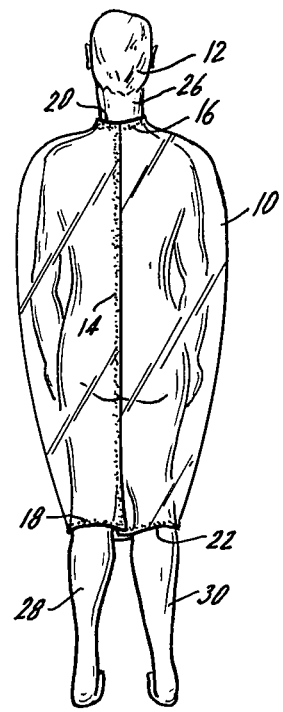
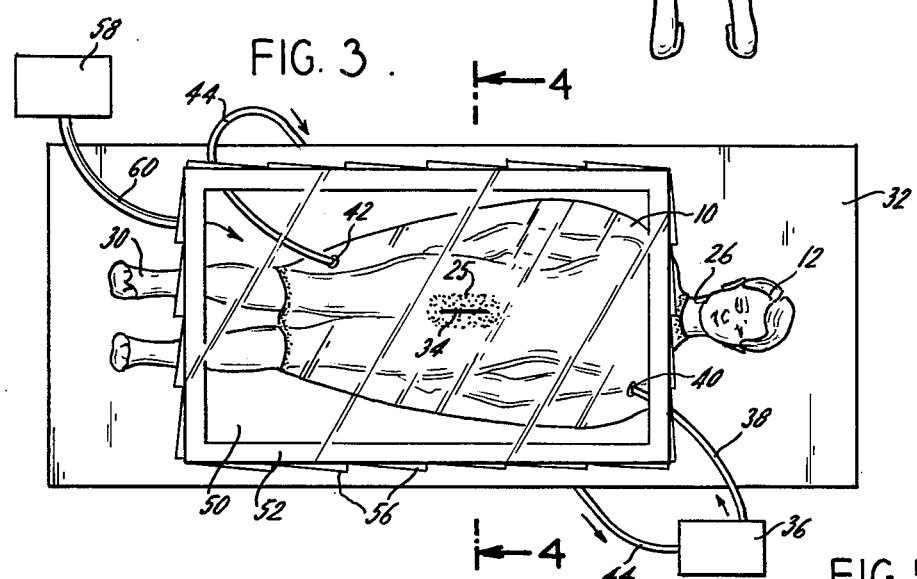
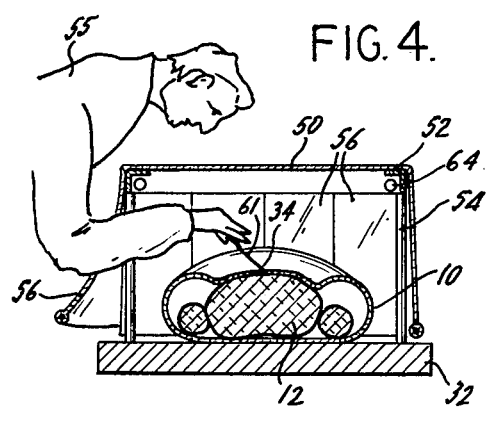
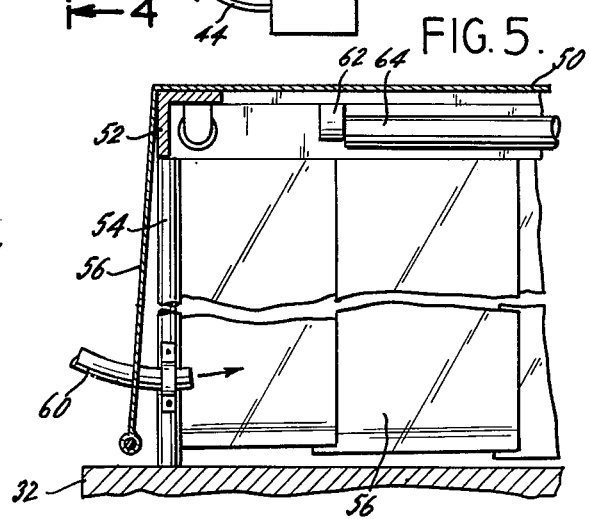

APPARATUS AND METHOD FOR PROVIDING AN ASEPTIC SURGICAL ENVIRONMENT

DESCRIPTION OF THE INVENTION

The present invention relates generally to sterilization procedures performed in an operating room to avoid patient infection, and more particularly to a procedure and system wherein a sterilized atmosphere is maintained about a substantial portion of the patient's body, as well as within a confined region including an incision site on the body so as to minimize risks of infection.

Present day techniques for maintaining a relatively germ free atmosphere in an operating room during the course of surgery typically involve costly apparatus for circulating filtered, sterile air throughout the room, and time consuming and expensive gowning or draping of both the patient and the operating room personnel with pre-sterilized coverings of one sort or another, e.g., surgeon's cap, mask, and even shoe covers. Because of this additional apparel, the operating room temperature is often reduced in order to increase the surgeon's comfort. It will be understood, however, that a relatively low temperature environment may not always be best for the patient. In particular, patients are known to sweat heavily after being covered by conventional, non-porous surgical drapes. Such patient sweating, combined with cold operating room temperatures, are known to frequently induce patient shock and thereby prevent the undertaking of further surgical procedures.

A known surgical procedure which attempts to reduce the extensive sterilization procedures employed up to now was developed under the sponsorship of Vickers Medical. In this procedure, an inflatable plastic isolator which has a surgical drape formed in its lower surface is placed over a patient lying on an operating table. A slightly positive pressure of sterilized air is supplied to the isolator to maintain it in an inflated condition. The bottom of the drape is brought over the patient and sealed against the patient's skin in the vicinity of an incision site by way of a germicidal adhesive. Surgeons then make incisions through the drape into the patient's body by inserting their hands through sleeved gloves formed in the sides of the isolator, working with sterilized instruments presented to them through an opening at one end of the isolator. It will be appreciated, however, that such a system requires relatively cumbersome support apparatus for maintaining the inflated isolator steady, as the surgical team manipulate instruments and other surgical supplies over the patient's body, during the course of an operation. Moreover, except for that portion of the patient's body which is sealed to the drape, the patient is exposed to an unsterilized environment during the operation. This may well result in an infection developing after the operation is completed and the isolator is drawn away from contact with the patient's body.

U.S. Pat. No. 2,473,033 also relates to apparatus for maintaining a sterilized atmosphere in the vicinity of an incision site on a patient's body. The patent discloses a bellows type structure which is lowered over the patient to present a soft rubber membrane, which seals the bottom of the structure, against the incision site. A surgeon then introduces his hands and arms through sleeved gloves extending into the structure, and makes incisions through the membrane into the patient's body. However, as with the isolator described above, the remainder of the patient's body is exposed to the operating room environment, thereby presenting a serious risk of infection when the bellows structure is withdrawn.

It is an object of the present invention to overcome the above and other shortcomings in conventional surgical procedures for providing an aseptic environment in which to perform an operation on a patient.

It is another object of the present invention to provide a surgical procedure and system wherein aseptic operating conditions are realized with a minimal expenditure of time and effort.

It is yet another object of the present invention to provide a surgical procedure and system wherein the patient is afforded maximum comfort.

It is yet a further object of the present invention to provide a surgical procedure and system wherein the patient is surrounded by a sterile atmosphere of controlled temperature and humidity, thereby significantly reducing patient sweating and resultant shock when the patient is moved into a low temperature environment such as an operating room.

It is still another object of the present invention to provide a surgical procedure and system wherein the chances of infections arising from staphylococcus for other bacteria originating from the patient's own body and from operating room personnel are substantially minimized.

In accordance with the present invention, a method of providing an aseptic environment about an incision site on a patient's body includes enveloping at least a portion of the patient's body including the incision site with a flexible film layer. The film layer is sealed against the patient's body remote from the incision site thereby defining a first region between the film layer and the body. The film layer is also sealed proximate the incision site on the patient's body. A first sterile atmosphere is provided within the first region, and a second sterile atmosphere is provided within a second region which is substantially adjacent the patient's body proximate the incision site.

A system for providing an aseptic environment about an incision site on a patient's body includes a flexible plastic film sheet, the sheet being constructed and arranged to be wrapped about and sealed to the patient's body remote from the incision site. A first region is thereby defined between the film layer and the body. Supply means provides a sterile atmosphere within the first region. Means are supported about the incision site for defining a second region which is substantially adjacent the patient's body surrounding the incision site. Supply means also provides a sterile atmosphere within the second region.

The above brief description, as well as further objects, features and advantages of the present invention, will be more fully understood by reference to the following detailed description of a presently preferred but nonetheless illustrative embodiment in accordance with the present invention, when taken in conjunction with the accompanying drawing, wherein:

FIG. 1 is a rear elevational view of a plastic film sheet dimensioned and contoured to be wrapped about a patient's body, the sheet having deposits of adhesive thereon, in accordance with the present invention;

FIG. 2 is a rear elevational view showing the sheet of FIG. 1 secured about the patient and adhesively sealed to the patient's neck and legs;

FIG. 3 is a top plan view of the patient of FIG. 2 lying on an operating table with the plastic sheet coupled to a supply of sterile gas, and showing an enclosure supported about the patient's body including an incision site thereon;

FIG. 4 is a cross-sectional right side elevational view taken substantially along line 4—4 in FIG. 3, and looking in the direction of the arrows, showing a surgeon operating on the patient by extending his arms through flaps formed on the sides of the enclosure;

FIG. 5 is an enlarged, fragmentary cross-sectional front elevational view taken through the lefthand portion of the enclosure as shown in FIG. 3, showing means within the enclosure for illuminating the operating site;

Figure 6:
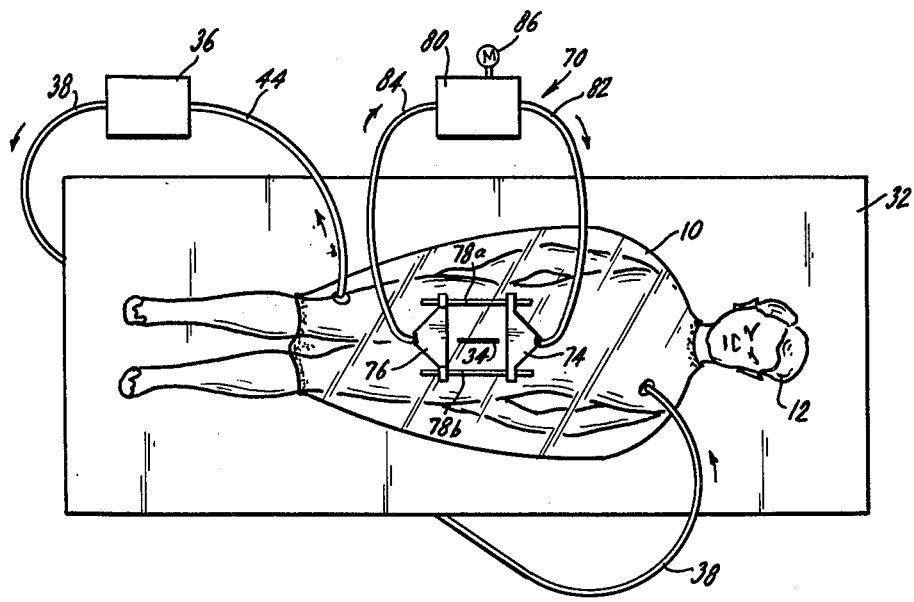
FIG. 6 is a top plan view showing the patient of FIG. 2 lying on an operating table while enveloped by the plastic sheet, and showing a pair of nozzles which can be substituted for the enclosure of FIGS. 3-5, the nozzles maintaining a laminar sterile flow of air or inert gas directly over the incision site on the patient in accordance with the present invention.

Referring now in detail to the drawing, and initially to FIGS. 1 and 2 thereof, there is shown a plastic film sheet 10 in accordance with the present invention. Sheet 10 is composed of pinhole-free polyethylene film which, for example, can be about 1.4 mil (0.04 mm) thick and composed of 60% low density resin having a specific gravity between 0.918 and 0.920, and a melt index of 2.0; 30% high clarity polyethylene resin of 0.925 specific gravity and 3.0 melt index; and 10% antistatic polyethylene resin such as that obtainable under the well-known trade name "AMPECET". However, other equivalent film compositions can be used for the sheet 10, provided they possess comparable strength, resiliency and clarity.

The film composition is then blown, stamped or die cut, and folded to conform to an overall configuration which facilitates its being wrapped about a patient 12, as shown in FIG. 2. An adhesive deposit 14 is provided on one of the rear confronting ends of the sheet 10 so that, when these ends are overlapped, they can be pressure sealed by way of the adhesive deposit. Additional adhesive deposits 16 and 18 are provided at opposite ends 20 and 22 of the sheet, respectively. Yet another adhesive deposit 24 may be provided to ensure proper sealing of the sheet 10 about the patient, as shown in FIG. 2. All of these deposits 14, 16, 18 and 24 should be shielded by release paper which can be removed at the time when the sheet 10 is wrapped about the patient as in FIG. 2, and located on the sheet 10 so as to be remote from any incision sites to be established on the patient's body. A suitable adhesive composition is one supplied by Franklin Chemicals under the name "COVINAX" No. 172.

Before the sheet 10 is completely sealed about the patient, however, a deposit of a conventional pressure sensitive bactericidal adhesive is placed on the patient's body over an operating area which includes a site where an incision is to be made. Such a deposit is illustrated by the stippling at 25 in FIG. 3. Once the sheet 10 is sealed about the patient, it is then pressed down over each of the adhesive deposits on the body which include an incision site. With the sheet 10 sealed about the patient's extremities such as his or her neck 26 and legs 28, 30, as shown in FIG. 2, a substantially closed region between the inside surface of the film sheet and the patient's body is created. Moreover, each operating area is aseptically isolated from the remainder of the patient's body, thereby providing a substantial barrier to staphylococcus bacteria which might otherwise migrate into an open incision.

Referring now to FIG. 3, the patient 12 is shown lying supine on an operating table 32, with the sheet 10 adhesively sealed at 25 to the patient's body and bordering an incision site 34 where a cut is to be made through the sheet 10 directly into the patient's body. A supply of sterile air is circulated through the region enclosed by the sheet 10 by way of an air supply unit 36 which may include a 1/10 to ¼ horsepower motor blower, a heating coil and a bacterial filter. The air supply is delivered at a relatively low pressure of about 1½ pounds per square inch through a flexible tube 38 which, in turn, is coupled to an inlet port 40 formed through the sheet 10 in the vicinity of the patient's shoulder area, for example. This air supply then circulates through the region enclosed by the sheet 10, over the patient's body, and exits through an outlet port 42 formed through the sheet 10 in the vicinity of the patient's legs, for example. The treated air is then returned to the supply unit 36 by way of a flexible return tube 44 coupled to the port 42. A flow of dry, heated air from the unit 36 will alleviate patient sweating and discomfort normally experienced during surgery. Of course, the inlet and outlet ports 40, 42 may be located other than as shown, provided they enable the sterile air to be circulated about a substantial portion of the patient's body which is enclosed by the sheet 10.

Normally, the sheet 10 should not rise more than about three inches from the patient's body while air is circulated therein by the unit 36. This will enable the passage of surgical tools to and from the incision site 34 with minimum interference from the raised sheet. It will be understood that the height to which the sheet 10 will rise is determined by the dimensions of the sheet relative to those of the patient's body, as well as by the air pressure maintained by the supply 36.

Referring to both FIGS. 3 and 4, a clear plastic canopy or tent enclosure 50 is supported about the patient's body by way of a frame 52 which stands on legs 54, the legs 54 resting on the surface of the operating table 32 on either side of the patient 12. The legs 54 support the enclosure frame 52 a sufficient height above the patient's body to provide a working clearance for the hands of a surgeon 55 and tools when placed inside of the enclosure 50, as explained in further detail below.

A suitable plastic material for enclosure 50 is a crystal clear polyethylene which may have, for example, a density of between 0.958 and 0.965, and a melt index of between 0.3 and 0.7. The sides of the enclosure 50 are formed by successive, overlying vertically hung strips 56 of the plastic material, each of the strips 56 being weighted at its bottom to maintain it in a normally vertical orientation.

A relatively low positive pressure of heated, sterilized air, nitrogen, argon, or other suitable gas is pumped into the enclosure 50 from a source 58 such as a tank of compressed gas via tube 60. It is also possible to supply sterilized air through the tube 60 from the supply unit 36 used in association with the patient enveloping sheet 10.

As shown in FIG. 4, the vertical strips 56 on the sides of the enclosure 50 can be parted to allow ingress of a surgeon's arms and hands to perform an operation, while a sterile atmosphere is still maintained closely adjacent to the patient's body including the incision site 34. Even though the enclosure 50 is not air tight, a constant outward flow of nitrogen, sterile air or like gas under positive pressure from the source 58 will prevent germs or other fine contaminants outside the enclosure 50 from entering therein. The surgeon 55, wearing sterile gloves, may then cut directly through the sheet 10 with a scalpel 60 to make the incision. A sterile environment is at all times maintained about the incision, the enclosure 50 acting as a barrier against germs originating from the surgeon's mouth and nose, as well as from all other sources outside the enclosure 50.

It will be appreciated that the upper polyethylene surface of the enclosure 50 might glare in the event external lighting is relied upon to illuminate the area of the incision site 34 on the patient. As shown in FIG. 5, this problem can be overcome by providing one or more lighting fixtures 62 with associated lamps 64 to illuminate the interior of the enclosure 50 a sufficient amount to make the operating site clearly visible. Those skilled in the art will understand that such lighting fixtures must be explosion proof and comply with all applicable rules and regulations governing the use of lighting fixtures in an operating room environment, where relatively high levels of pure oxygen might be present.

Figure 7:
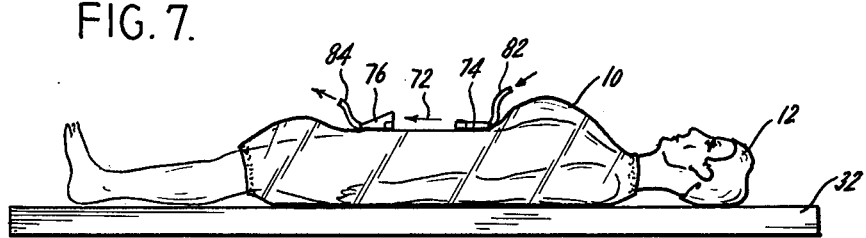
FIG. 7 is a front elevational view of the patient on the operating table as in FIG. 6, showing further details of the nozzles.

Referring now to FIGS. 6 and 7, there is shown apparatus 70 for providing a sterile laminar flow 72 directly over the incision site 34 on the patient's body, and is usable in place of the enclosure 50 and its associated equipment in FIGS. 3-5 to provide an aseptic barrier against bacteria or other matter present in the operating room environment from entering the incision.

Basically, apparatus 70 includes a pair of nozzles 74 and 76, respectively, which are initially positioned in confronting, spaced-apart relationship about the incision site 34 by way of a pair of alignment guides 78a, 78b. The guides 78a, 78b, which extend through openings in respective ends of the nozzles 74, 76, are removed once the nozzles are taped in place, as explained below in connection with FIG. 8. Nozzle 74 diffuses the sterile air from an elongated opening which is typically about one-half inch in height by about eight inches in width. Nozzle 76 collects the air flow through an elongated opening which is typically about two inches in height and also about eight inches in width.

In addition, the apparatus 70 includes a blower and filter unit 80 which is coupled by flexible tubes 82 and 84 to nozzles 74 and 76, respectively. The unit 80 is driven by a motor 86 to which it is detachably coupled so that the unit 80, and the remaining components of the apparatus 70, can be discarded after use and a new, sterilized set of components used with the same motor 86 for each surgical procedure to be undertaken. Thus, with the exception of the motor 86, all components of the apparatus 70 can be made of plastic or other like, relatively inexpensive material.

Figure 8:
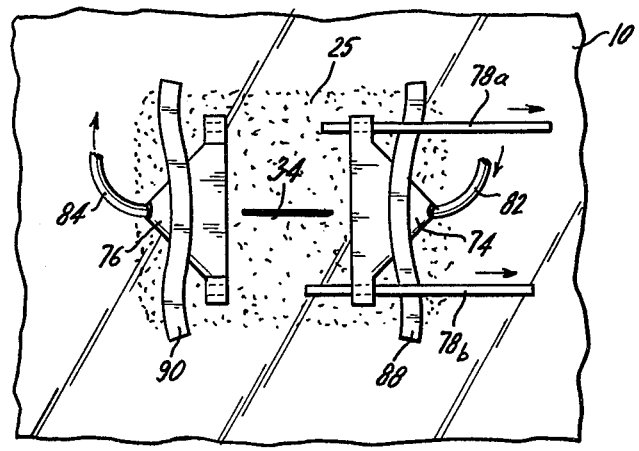
FIG. 8 is an enlarged, detail fragmentary top plan view of the pair of nozzles taped against the sheet about the incision site, and a pair of alignment rods for locating the nozzles.

Apparatus 70 can be readily placed into operation by aligning the nozzles 74, 76, with the aid of guides 78a, 78b, about incision site 34 and separating their confronting openings by an amount just sufficient to enable proper access to the site 34 by a surgeon. As shown in FIG. 8, nozzles 74, 76 are then positioned by strips of tape 88 and 90 against the plastic sheet 10 on the patient's body. It will be recalled that a germicidal adhesive is provided under the plastic sheet 10 on the patient's body over an area including the incision site 34. Accordingly, the nozzles 74, 76 should be taped to the sheet 10 only where the sheet is adhesively secured to the patient's body, as shown by the stippling at 25, thereby ensuring that the nozzles will remain fixed relative to the incision site.

Instead of supplying sterile air, unit 80 may provide inert gases such as helium, nitrogen, or argon, if desired or a bactericidal mist in air. In any event, further constructional details of unit 80 are such as would be obvious to one skilled in the art, and are therefore not shown in the drawings.

The surgical procedure of the present invention is especially desirable in orthopedic surgery and severe burn cases. In the former, where only a small amount of blood normally circulates about the skin opening, staphylococcus infections arising from germs present on the surrounding skin areas are quite common. The sealing of the sheet 10 about the incision site 34 with a bacteriacidal adhesive prevents such migration of germs into the opening while surgery is performed. In the burn cases, it is desirable to maintain a medicinal atmosphere closely adjacent to the patient's body rather than a bandage which might further injure the skin. With the present invention, the supply unit 36 used for circulating air or other gases through the sheet 10 can be constructed to provide a medicated, as well as temperature and humidity controlled atmosphere, according to construction techniques and procedures well known to those skilled in the field.

Another significant advantage realized by the present invention is the elimination of the need for costly operating room air sterilization equipment of large air handling capacity. Instead, smaller units which need only filter and circulate a volume of air sufficient to fill the region between the patient 12 and the enveloping sheet 10, and to accommodate the enclosure 50 or laminar flow apparatus 70 of the present invention can be used at great savings.

Both the plastic film sheet 10 and the plastic material defining the enclosure 50, or the laminar flow apparatus 70 can be supplied as presterilized, relatively inexpensive disposable items, thereby reducing laundering and equipment costs. Also, the surgical team need don nothing more than sterile gloves to perform an operation once the supply units 36, 58 or 80 are turned on, thus significantly reducing their preparation time and affording them greater freedom of movement once the operation proceeds.

As will be readily apparent to those skilled in the art, the present invention may be used in other specific forms and for other purposes without departing from its spirit or essential characteristics. For example, the enclosure 50 may have relative proportions and dimensions other than those suggested in the drawing, a variety of configurations being made to accommodate various types of surgery at different locations on the patient's body. Further, the enclosure 50 may be supported by ceiling hangers or by legs extending down alongside the operating table 32, rather than resting on the table, as shown in the drawings.

Additionally, the deposit of adhesive 25 can be replaced by other equivalent means which provides a germicidal barrier between the incision site 34 and the adjacent operating area on the patient's body, it not being necessary that the film sheet 10 be brought into direct contact with the patient's skin over the entire operating area by such an adhesive.

In its broader aspects, the present invention contemplates a method which allows a surgeon to operate under aseptic conditions at an operating area on a patient's body when the patient is in an operating room, including the steps of enveloping a portion of the patient's body including the operating area with a first sterile atmosphere, and further enveloping the first sterile atmosphere with a second sterile atmosphere, whereby the surgeon initially enters the second sterile atmosphere and proceeds into the first sterile atmosphere to access the operating area on the patient's body.

The present embodiment is, therefore, to be considered as illustrative and not restrictive, the scope of the invention being indicated by the claims rather than by the foregoing description, and all changes which come within the meaning and range of equivalents of the claims are therefore intended to be embraced therein.

What is claimed is:

1. A method of providing an aseptic environment over an incision site on a patient's body comprising the steps of completely enveloping at least the portion of the patient's body which includes said incision site with a flexible plastic film layer, adhesively attaching and thereby sealing said film layer to said patient's body remote from said incision site and adhesively attaching and thereby sealing said film layer to said patient's body proximally surrounding said incision site so as to form a region between the remote and proximal seals, the film layer, and the patient's body remote from said incision site, providing a circulating first sterile atmosphere within said region, enveloping said region and said incision site with a flexible plastic layer which isolates said region and said incision site so as to form a volume therebetween, and conditioning and providing a second circulating sterile atmosphere within said volume.

2. The method of claim 1 further including the step of medicating said first sterile atmosphere.

3. The method of claim 1 wherein the step of adhesively attaching said film layer to said patient's body proximally surrounding the incision site is performed with a bacteriostatic adhesive.

4. The method of claim 1 or 2 further including the step of controlling the temperature and relative humidity of said first sterile atmosphere.

5. Apparatus for providing aseptic conditions about a proposed incision site on a patient's body comprising a first barrier for enveloping and isolating the proposed incision site, said first barrier comprising a flexible sheet of plastic film, said film being of a size for wrapping entirely about the patient's body, means for adhesively attaching said flexible sheet to said patient's body remote from and at and proximally surrounding the incision site, means for creating a first circulating conditioned sterile atmosphere between said first barrier and the patient's body, a second barrier enveloping said first barrier, and means for creating a second sterile atmosphere between said first barrier and said second barrier, said second barrier being constructed and arranged so that a surgeon may reach through said second barrier and operate through said first barrier by cutting said first barrier to obtain access to the proposed incision site.

6. The apparatus of claim 5 wherein said first sterile atmosphere is medicated.

7. The apparatus of claim 5 wherein said second sterile atmosphere includes a laminar flow section.

8. The apparatus of claim 5 wherein said means for adhesively attaching said flexible sheet comprises a bactericidal adhesive.

9. The apparatus of claim 5 wherein said second barrier comprises a canopy enclosure.

10. The apparatus of claim 5 or claim 9 wherein said second sterile atmosphere is maintained at a positive pressure with respect to the surrounding environment.

* * * * *